United States Patent [19]

Bacskai

[11] 4,123,605

[45] Oct. 31, 1978

[54] META-ISOCYANATOBENZYL ISOCYANATE-DERIVED POLYURETHANES

[75] Inventor: Robert Bacskai, Kensington, Calif.

[73] Assignee: Chevron Research Company, San Francisco, Calif.

[21] Appl. No.: 814,587

[22] Filed: Jul. 11, 1977

Related U.S. Application Data

[62] Division of Ser. No. 422,623, Dec. 7, 1973, Pat. No. 4,079,073.

[51] Int. Cl.$^2$ .................. C08G 18/42; C08G 18/48; C08G 18/14
[52] U.S. Cl. .................................. 528/60; 521/157; 521/174; 528/65; 528/66
[58] Field of Search ...... 260/2.5 AT, 75 NK, 75 NT, 260/77.5 AT

[56] References Cited

U.S. PATENT DOCUMENTS

| 3,252,942 | 5/1966 | France | 260/2.5 AT |
|---|---|---|---|
| 3,305,574 | 2/1967 | Zecher et al. | 260/77.5 AT |
| 3,448,139 | 6/1969 | Farrissey et al. | 260/2.5 AT |

*Primary Examiner*—V. P. Hoke
*Attorney, Agent, or Firm*—D. A. Newell; John Stoner, Jr.; A. T. Bertolli

[57] ABSTRACT

A novel chemical compound is disclosed, namely meta-isocyanatobenzylisocyanate (MIBI). MIBI can be used to form useful polyurethane materials, particularly polyurethane coating materials.

5 Claims, No Drawings

META-ISOCYANATOBENZYL ISOCYANATE-DERIVED POLYURETHANES

This is a division of application Ser. No. 422,623, filed Dec. 7, 1973, now U.S. Pat. No. 4,079,073, issued Mar. 14, 1978.

BACKGROUND OF THE INVENTION

The present invention relates to a novel isocyanate compound and materials made using the compound.

Isocyanates are organic compounds having the structure N=C=O, as opposed to the cyanate structure CNO. Aryl isocyanates, Ar—N=C=O, can be made by the reaction of phosgene on aryl amines, for example:

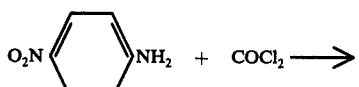

p-Nitroaniline Phosgene

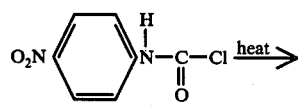

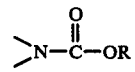

p-Nitrophenyl isocyanate

Isocyanates react with alcohols to give carbamates (urethanes) and with primary and secondary amines to give substituted ureas. For example:

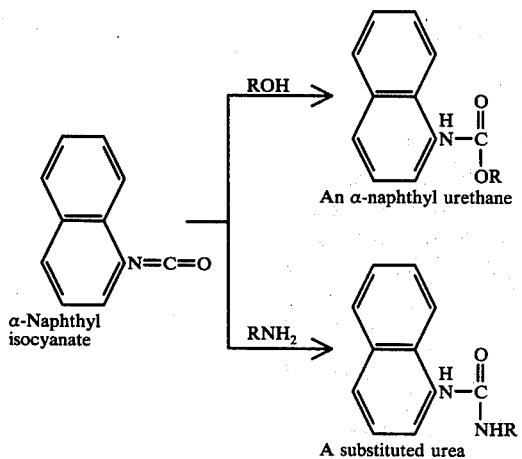

Numerous diisocyanates have been disclosed for producing polyurethanes. For example, the following diisocyanates are disclosed for such purposes in "High Polymers — Polyurethanes — Chemistry and Technology," Vol. XVI, Part I (Chemistry), Saunders and Frisch, Interscience Publishers, 1962: tolylene diisocyanate (TDI); 4,4'-diphenylmethane diisocyanate (MDI); 1,6-hexamethylene diisocyanate (HDI); 1,5-naphthalene diisocyanate (NDI); 3,3'-dimethoxy-4,4'-biphenyl diisocyanate (DADI); 3,3'-dimethyl-4,4'-biphenyl diisocyanate (TODI); phenylene diisocyanate (PDI); and 4,4'-biphenyl diisocyanate (XDI).

The term "polyurethane" is used herein to mean those polymers which contain a significant number of urethane groups. Usually polyurethanes are obtained by the combination of a polyisocyanate with reactants which have at least some hydroxyl groups, for example, polyether polyols, castor oil and simple glycols. Other reactive groups may also be present, such as amino and carboxyl groups. Thus, a typical 37 polyurethane" can contain, in addition to urethane groups, aliphatic and/or aromatic ester, ether, amide and urea groups. These polymers are also sometimes called simple "urethanes".

Urethanes or polyurethanes can be considered to have the group which is an ester of the unstable carbamic acid, or amide esters of carbonic acid:

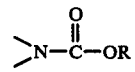

and the urethane group has the characteristic configuration:

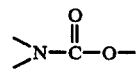

Thus a polyurethane has a significant number of these urethane groups, although not necessarily repeating in a regular order.

Formulations and conditions for preparation of polyurethanes are known in the art. See, for example, Part I of Saunders et al, cited above. Further formulations and uses for various polyurethane materials are given in Saunders et al, Part II of the above Vol. XVI (Technology).

Para-isocyanatobenzylisocyanate (PIBI) is disclosed in Liebigs "Annalen der Chemic," Vol. 562, p. 126. Metaisocyanatobenzylisocyanate (MIBI), however, has not been disclosed in the art.

SUMMARY OF THE INVENTION

According to the present invention there is provided a new chemical compound, namely meta-isocyanatobenzylisocyanate.

Among other factors, the present invention is based on my discovery of the new compound MIBI and my finding that MIBI has unexpected, advantageous properties when used to produce polyurethanes, particularly when used to produce polyurethane coating materials.

As indicated above, polyurethane materials and methods for producing polyurethanes are well known in the art. The Saunders et al references, previously cited, describe general formulations and conditions for producing polyurethanes for flexible and rigid foams, elastomers, coatings, adhesives, and fibers. In general, the methods disclosed in the prior art such as the Saunders et al references for making various polyurethanes can be used with MIBI instead of the diisocyanates specified, for example, in the Saunders et al references.

Thus, in accordance with a preferred embodiment of the present invention, there is provided a polyurethane made by reacting MIBI with a polyfunctional alcohol having a molecular weight of at least 92.

The term "polyfunctional alcohol" is used herein to mean an organic material containing at least two —OH groups which will react with an isocyanate such as MIBI to produce a polyurethane. Exemplary polyfunctional alcohol materials include those polyols disclosed, for instance, in U.S. Pat. No. 3,759,873 at col. 3 and col. 4, and hydroxyl-terminated polyesters, polyether diols and triols, and hydroxyl-terminated hydrocarbon polymers as described, for example, in "Polyurethane Technology," ed. P. F. Bruins, Wiley, 1969, pp. 12-18, shown below:

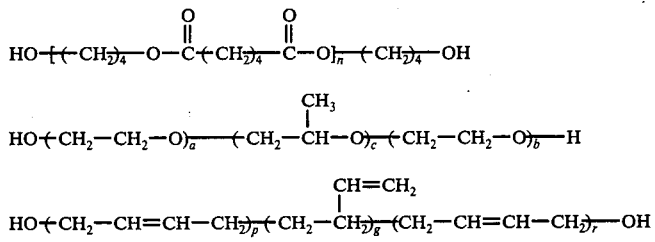

I have found that polyurethane coating materials prepared using MIBI have unexpected advantages over coating materials similarly prepared using PIBI. Thus, in accordance with a particularly preferred embodiment of the present invention there is provided a polyurethane coating composition made by reacting MIBI with a polyfunctional alcohol having a molecular weight of at least 92, under conditions sufficient to obtain a coating material suitable for application as a paint constituent or varnish constituent or substitute.

The term "coating material" is used herein to include the material before it is applied to a surface to form a coating, as well as including the resulting coating after drying. The coating typically is formed on applying to a surface and allowing excess isocyanate to react with moisture in the air to form substituted urea groups. The coating material can be used as a constituent of a paint. As is known in the prior art, the isocyanate-containing material is compatible with other film-forming materials, and may be combined or mixed therewith to give new coating compositions. Although the polyurethane coating compositions produced in accordance with the present invention can in general be used in various paints, preferably the polyurethane compositions provided in accordance with the present invention are used to form a varnish substitute material, that is, a material which will form a reasonably translucent coating upon application to a surface.

In general, urethane coating compositions can be prepared from MIBI by the usual technique of converting a diisocyanate to a "prepolymer." This is accomplished by reacting 2 equivalents of MIBI with 1 equivalent of a polyhydroxy compound, e.g., a polyether polyol, or polyester polyol, etc. Conveniently, the prepolymer is prepared in a solvent and stored in that solvent until it is applied. Frequently a catalyst is added to the system to shorten reaction times. Such catalysts include compounds of tin, lead, bismuth, potassium, etc.

A coating composition was prepared from MIBI in the following way: 1 equivalent of a commercial polyether triol (e.g., Pluracol TP-1540, eq. wt. = 504, Wyandotte Chemical Corp.), 2 equivalents of MIBI and 0.16 weight percent of dibutyl tin dilaurate catalyst are mixed at room temperature in 50 weight percent of xylene/amylacetate (9/1). After standing at room temperature for 4-20 hours, the resulting viscous solution can be applied to a substrate by conventional techniques, such as brushing, spraying, doctor blade, etc.

Another outstanding and completely unexpected property of MIBI is its high reactivity as compared to other well-known diisocyanates. I found that MIBI reacts faster with alcohols than does either tolylene diisocyanate (TDI) or meta-xylylene diisocyanate (MXDI). Furthermore, prepolymers made from MIBI have faster gel times than those made from either TDI or MXDI. On the basis of the above observations, MIBI appears to be about 5 times more reactive than TDI and about 2 times more reactive than MXDI, whereas, since MIBI has one aryl isocyanate group (compared to two for TDI) and one benzyl isocyanate group (compared to two for MXDI), intermediate reactivity was expected. Fast reaction times are very advantageous in many applications, especially wherein the subsequent manufacturing steps must wait for coating to harden or foam to form, etc.

I have also found that good polyurethane foams can be prepared using MIBI. Thus, in accordance with the present invention there is provided a polyurethane foam material made by reacting MIBI with a polyfunctional alcohol having a molecular weight of at least 92 under conditions sufficient to obtain a foam material or a material which can be converted to a foam by reaction with water.

In general, foam preparation is similar to methods disclosed in the aforesaid Saunders et al references for preparation of polyurethane foams, except that MIBI is used in place of the diisocyanates disclosed in the Saunders references.

EXAMPLES AND FURTHER DESCRIPTION

MIBI can be prepared from the corresponding diamine by reaction with phosgene as follows:

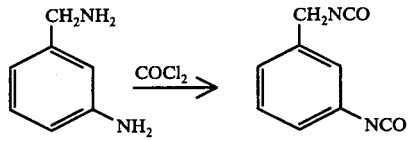

Suitable reaction conditions for preparing MIBI according to the above reaction are the same as used to convert other diamines to diisocyanates. In general, the diamine or the diamine hydrochloride, neat or in a suitable solvent such as dichlorobenzene, ethylacetate, etc., is contacted with phosgene at elevated temperatures in the range of 75° to 150° C. for a period of time sufficient to effect conversion of the amine groups to isocyanate groups. The product is recovered by removal of the solvent followed by distillation. MIBI has a boiling point of 104°-105° C. at 1 mm pressure.

In my concurrently filed applicated entitled "Diamine Preparation," there is also disclosed a method for making metaaminobenzylamine from meta-nitrobenzonitrile, which in turn can be prepared from benzonitrile. The disclosure of my aforesaid application on diamine preparation is incorporated by reference herein.

EXAMPLE 1

Preparation of meta-isocyanatobenzylisocyanate (MIBI)

A 2-liter, 3-necked flask equipped with a stirrer, condenser, addition funnel, thermometer and gas inlet tube was charged with 500 ml o-dichlorobenzene and 305 g phosgene. A solution of 30.5 g (0.25 mol) m-aminobenzylamine in 450 ml o-dichlorobenzene was added with stirring in 35 minutes, while maintaining the temperture in the flask between $-3°$ and $+5°$ C. by external cooling. The resulting white precipitate was stirred for an additional hour at room temperature. The reactive mixture was heated in a phosgene stream to 130° C. and maintained at that temperature for 5 hours. During this time, 200 g of phosgene was added. Following phosgenation, the resulting solution was cooled to room temperature, purged with nitrogen, and the solvent was removed by vacuum distillation. Continued vacuum distillation of the residue yielded a liquid fraction which contained 26.3 g MIBI (0.151 mol, 60.5% of theory). Redistillation yielded 99.17% pure MIBI (by vapor-phase chromatography); boiling point 104°–105° C. at 1 mm. Elemental analysis showed: %C, calc. 62.07, found 61.89, 61.93; %H, calc. 3.47, found 3.57, 3.53; %N, calc. 16.08, found 16.33, 16.22. Nuclear magnetic resonance analysis showed peaks at 6.89–7.38 ppm (aromatic portions) and 4.46 ppm ($CH_2$ protons) downfield from tetramethylsilane, and aromatic/$CH_2$ = 2.08/1 (calc. = 2/1). Infrared spectra showed a peak at 2260 $cm^{-1}$ (NCO absorption).

EXAMPLE 2

Preparation of para-isocyanatobenzylisocyanate (PIBI)

For comparison, para-isocyanatobenzylisocyanate was prepared by the same general technique as described in Example 1. Purity of PIBI by vapor-phase chromatography = 100%. Boiling point was 92°–104° C. at 0.7–0.8 mm. Elemental analysis showed: %C, calc. 62.07, found 62.10, 62.25; %H, calc. 3.47, found 3.53, 3.51; %N, calc. 16.08, found 15.89, 16.05. Nuclear magnetic resonance showed peaks at 6.93–7.30 ppm (aromatic protons) and 4.43 ppm ($CH_2$ protons) downfield from tetramethylsilane, and aromatic/$CH_2$ = 2.05/1 (theory = 2/1).

EXAMPLE 3

Comparative reactivities of MIBI, TDI and metaxylylene diisocyanate (MXDI)

The activity of diisocyanates towards alcohols was determined by mixing the corresponding diisocyanate, alcohol and dibutyl tin dilaurate in benzene and recording the —NCO absorbance (2260–2270 $cm^{-1}$) in the infared as a function of time. The results, expressed as "90% reaction" (the time when 90% of the originally present NCO groups disappeared) are summarized in Table I. The experimental conditions and concentrations of the reactants were: temperature, 25° C.; solvent, benzene; diisocyanate, 32 mmols/liter; 1-butanol, 575 mmols/liter, 2-propanol, 575 mmols/liter, and dibutyl tin dilaurate, 0.17 mmols/liter.

TABLE I

| Reaction with 1-butanol | 90% reaction (minutes) |
| --- | --- |
| MIBI | 6.0 |
| MXDI | 10.7 |
| TDI | 29.2 |
| Reaction with 2-propanol | |
| MIBI | 25.5 |
| MXDI | 37.5 |
| TDI | 136 |

EXAMPLE 4

Gel times of polyurethanes prepared with various diisocyanates

In a series of experiments, 1 meg. portions of a commercial polyether polyol (PPG 2025, eq. wt. = 992; Union Carbide Corp.), containing 0.5 weight percent dibutyl tin dilaurate was mixed with 1.1 meg. portions of MIBI, MXDI and TDI, respectively. On standing at room temerature, the solutions became gradually more viscous. The times required for the reaction mixtures not to flow were recorded as polyurethane gel times. The gel times of the polyurethanes obtained with the 3 diisocyanates are summarized in Table II.

TABLE II

| Polyurethane Gel Times | |
| --- | --- |
| Diisocyanate | Gel time (minutes) |
| MIBI | 90 |
| MXDI | 140 |
| TDI | 315 |

EXAMPLE 5

Polyurethane coatings from MIBI, PIBI & TDI

Isocyanate prepolymers suitable for the preparation of polyurethane coatings were prepared by the method discussed in "Polyurethane Technology," supra, p. 250. Thus, 126 parts of commercial polyether triol (Pluracol TP-1540, eq. wt. = 504, Wyandotte Chemical Corp.) containing 0.262 weight percent dibutyl tin dilaurate was mixed with 44 parts diisocyanate in 152 parts of xylene and 17 parts of amylacetate. On standing at room temperature, the solution become viscous. Using a 0.006 inch Doctor blade, films were cast from the prepolymer solution onto aluminum plates. The time required for the coating to lose its tackiness (touch by finger), called "cure time," was recorded. Ten days after preparation, the coatings were exposed in a weatherometer. The weatherometer tests were carried out in a black-walled weatherometer at a temperature in the range 140°–150° F. on a cycle of 102 minutes of light and 18 minutes of light + water. After 280 hours, the color and appearance of the coatings were recorded. The results obtained with polyurethane coatings prepared from MIBI, PIBI and TDI are summarized in Table III.

TABLE III

| | Polyurethane Coatings from Diisocyanate Prepolymers | |
| --- | --- | --- |
| Diisocyanate in prepolymer | Cure time (min.) | Weatherometer exposure Color; Appearance |
| MIBI | 82 | Light yellow; transparent, no white spots |
| PIBI | 78 | Light yellow; non-transparent, many white spots, rough surface |
| TDI | 303 | Brown; transparent, no white spots |

EXAMPLE 6

Polyurethane foams from MIBI and TDI

One-shot flexible polyurethane foams were prepared by using the formulation (slightly modified) reported in "Handbook of Foamed Plastics," R. J. Bender editor, Lake Publishing Corp., 1965, p. 180, Table X-7. Thus a solution, designated as "A" in the following, was prepared by mixing 50 g of commercial polyether triol (Pluracol GP-3030, eq. wt. = 966, Wyandotte Chemical Corp.), 0.05 g dibutyl tin dilaurate, 0.25 g triethylenediamine, 0.5 g surfactant (Silicone Surfactant 193, Dow Corning Co.) and 1.95 g water. In a 150-ml plastic beaker, 2.5 g of Solution "A" was vigorously mixed for 15 seconds with 0.97 g of MIBI. Foaming started instantaneously, and in about 20 minutes 55 ml of nontack, flexible, colorless foam was formed. Under the same conditions, TDI gave 67 ml of colorless flexible foam. Using the same formulation, MXDI, although reacted, did not foam up. On standing at room temperaure for 37 days, the MIBI foam remained colorless, while the TDI foam turned yellow. After 84 days the MIBI foam was still white, whereas the discoloration intensity of the TDI foam increased.

What is claimed is:

1. A polyurethane composition made by reacting meta-isocyanatobenzylisocyanate wih a polyfunctional alcohol having at least two hydroxyl groups and a molecular weight of at least 92, under conditions sufficient to obtain a material useful as a coating material, as a paint constituent, as a varnish substitute, or as a foam.

2. A polyurethane composition according to claim 1 wherein the polyfunctional alcohol is glycol.

3. A polyurethane composition according to claim 2 wherein the glycol contains a minor amount of polyfunctional alcohol having at least three hydroxyl groups.

4. A polyurethane composition according to claim 1 wherein the polyfunctional alcohol has at least three hydroxyl groups.

5. A polyurethane composition according to claim 4 wherein the polyfunctional alcohol has a molecular weight between about 500 and 10,000.

* * * * *

UNITED STATES PATENT AND TRADEMARK OFFICE
CERTIFICATE OF CORRECTION

PATENT NO. : 4,123,605
DATED : October 31, 1978
INVENTOR(S) : Robert Bacskai

It is certified that error appears in the above-identified patent and that said Letters Patent are hereby corrected as shown below:

Column 2, line 10, "typical 37Polyurethane" should read --typical "polyurethane"--.

Column 2, line 13, "simple" should read --simply--.

Column 5, line 15, "temperture" should read --temperature--.

Column 5, line 36, "$CM^{31}$ $^{1}$" should read --$CM^{-1}$--.

Column 5, line 60, "$CM^{31}$ $^{1}$" should read --$CM^{-1}$--.

Column 5, line 61, "infared" should read --infrared--.

Column 6, line 15, "meg" should read --meq.--.

Column 6, line 18, "meg" should read --meq.--.

Column 6, line 44, "become" should read --became--.

Column 7, line 16, "nontack" should read --nontacky--.

Column 8, line 5, "wih" should read --with--.

Column 8, line 11, "is" should read --is a--.

Signed and Sealed this

Fifth Day of June 1979

[SEAL]

Attest:

RUTH C. MASON
Attesting Officer

DONALD W. BANNER
Commissioner of Patents and Trademarks